(12) United States Patent
Sattler et al.

(10) Patent No.: US 7,154,071 B2  
(45) Date of Patent: Dec. 26, 2006

(54) DEVICE FOR TRANSMITTING AN ELECTRIC SIGNAL DETECTED BY CONTACT WITH THE SKIN SURFACE

(75) Inventors: Frank Sattler, Lübeck (DE); Robert Sliepen, Aachen (DE)

(73) Assignee: Dräger Safety AG & Co. KGaA (DE)

( * ) Notice: Subject to any disclaimer, the term of this patent is extended or adjusted under 35 U.S.C. 154(b) by 0 days.

(21) Appl. No.: 11/211,032

(22) Filed: Aug. 24, 2005

(65) Prior Publication Data

US 2006/0122471 A1 Jun. 8, 2006

(30) Foreign Application Priority Data

Dec. 7, 2004 (DE) .................. 10 2004 058 819

(51) Int. Cl.
*H05B 1/02* (2006.01)
*A61B 5/08* (2006.01)

(52) U.S. Cl. .................. 219/497; 600/388; 600/509; 600/390

(58) Field of Classification Search ............. 219/494, 219/497, 506; 600/529, 388, 508, 382, 390
See application file for complete search history.

(56) References Cited

U.S. PATENT DOCUMENTS 5,078,134 A * 1/1992 Heilman et al. ............. 607/4

2003/0212319 A1 * 11/2003 Magill ..................... 600/382
2005/0054941 A1 * 3/2005 Ting et al. ................. 600/529

FOREIGN PATENT DOCUMENTS

GB 2 350 193 A 11/2000

* cited by examiner

*Primary Examiner*—Mark Paschall
(74) *Attorney, Agent, or Firm*—McGlew & Tuttle, PC

(57) ABSTRACT

A device for transmitting electric signals detected by contact with the skin surface to an evaluating unit. The device has a stack of at least two layers of clothing (3, 7) with an electric path or electric line connection (4, 8) through each of the layers of clothing (3, 7). The lowermost layer of clothing (3) is provided with an electrode (2) contacting the skin surface of the body (1) of the wearer of the clothing and with an electrically conductive surface (5) on the side facing away from the skin surface. Each additional layer of clothing (7) stacked on the lowermost layer of clothing (3) is provided with an electrically conductive surface (6, 9) each on the underside and the top side. A carrying belt (11) is led over the stack of layers of clothing (3, 7) is provided with an electrically conductive surface (10), which faces the topmost layer of clothing (7) and which is connected to the evaluating unit (14) by means of an electric line (12).

20 Claims, 1 Drawing Sheet

DEVICE FOR TRANSMITTING AN ELECTRIC SIGNAL DETECTED BY CONTACT WITH THE SKIN SURFACE

CROSS REFERENCE TO RELATED APPLICATIONS

This application claims the benefit of priority under 35 U.S.C. § 119 of German Application DE 10 2004 058 819.8 filed Dec. 7, 2004, the entire contents of which are incorporated herein by reference.

FIELD OF THE INVENTION

The present invention pertains to a device for transmitting an electric signal detected by contact with the skin surface to an evaluating unit.

BACKGROUND OF THE INVENTION

It is known that persons who must work in situations involving a high level of physical stress are monitored in respect to physiological parameters that are relevant for health. These include, for example, the heart rate (HR) or voltage potentials, which are measured on the skin surface and are evaluated for an ECG and thus reveal how the current personal health status is in terms of the heart and the circulation of the person being monitored, i.e., for example, the status of a firefighter during a firefighting mission. In case the current physical state appears to be absolutely life-threatening, an acoustically and/or optically perceptible alarm is triggered, or at least the mission command center is informed, so that corresponding measures can be taken.

The nondetachable connection by means of cables is known for the electrical contacting of the individual electrodes with the corresponding electronic ECG evaluating unit. The requirement is that the electrodes shall have been placed manually on the skin surface in advance. In case of a detachable connection by means of plug-in connections, the cables must likewise be led securely, and the establishment of the plug-in connections likewise requires additional steps. In addition, especially high requirements must be imposed on the plug-in connections in terms of safety and stability against fire, high temperatures, corrosive gases and other factors, for example, in the area of firefighting.

GB 2 350 193 A discloses a device for establishing an electric connection between two textiles, so that an electric signal, for example, for an ECG, is sent from one side of a fabric, which is in contact with the body surface, to the other side and is subjected to further processing there.

SUMMARY OF THE INVENTION

The object of the present invention is to provide a device for transmitting an electric signal detected by contact with the skin surface to an evaluating unit with an improved electric connection technique, which makes do without additional steps for the connection and without a plug.

According to the invention a device is provided for transmitting an electric signal detected by contact with the skin surface to an evaluating unit. The device includes a stack of at least two layers of clothing with an electric line connection through each of the layers of clothing. The lowermost layer of clothing (closest to the skin of the wearer) is provided with an electrode contacting the skin surface of the body of the wearer of the clothing and with an electrically conductive surface on the side facing away from the skin surface. Each additional layer of clothing that is stacked on (or above) the lowermost layer of clothing is provided with an electrically conductive surface each on the underside and the top side. A carrying belt is led over the stack of layers of clothing. The carrying belt is provided with an electrically conductive surface, which faces the topmost layer of clothing and which is connected to the evaluating unit by means of an electric line.

Using the device proposed, an electric connection is established between the electrode of the lowermost layer of clothing contacting the skin surface of the wearer of the clothing and the evaluating unit for the signals of the electrode rapidly and in a simple manner by putting on a plurality of pieces of clothing and the plurality of layers of clothing formed as a result and by finally leading a carrying belt over the stack of at least two layers of clothing.

The carrying belt may be connected to a respirator or respirator unit on the back of the wearer of the clothing, so that the weight of the respirator presses the carrying belt onto the stack of layers of clothing.

The lowermost layer of clothing may be provided with a plurality of electrodes, wherein one of the electrodes is a reference electrode for an ECG measurement.

The electrically conductive surfaces of the layers may have a size of a few square cm and may be oriented such that they overlap at least partially when the pieces of clothing associated with the layers of clothing are put on by the wearer of the clothing. The conductive surfaces of the layers may be bonded, welded, sintered, woven, embroidered, knitted or tufted. The conductive surfaces may be structured or designed in the form of Velcro fasteners (hook and loop fasteners) or as Velcro fasteners or regions of such adjacent to or surrounding the respective conductive surface, so that the position of the individual layers of clothing and of the carrying belt in relation to one another and to the conductive surfaces can be fixed.

The electric line that carries a signal from the electrically conductive surface, which faces the topmost layer of clothing to the evaluating unit may be integrated within the carrying belt. The evaluating unit may be connected to a mission command center in a wireless manner.

The electric line connection through each of the layers of clothing may be electrically conductive threads and plug-in or push contact elements, which contact through one or more said layers of clothing. The electric line connection through the layers of clothing may be provided with the clothing having holes or openings with cut-out patterns, so that the electrode and/or the electrically conductive surfaces can be electrically contacted through the layers of clothing.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The only FIGURE is a schematic view showing a device for transmitting an electric signal detected by contact with the skin surface according to the invention, showing a reference electrode with a plurality of pieces of clothing with associated layers of clothing and a carrying belt for a respirator.

DESCRIPTION OF THE PREFERRED EMBODIMENTS

Figure 1:
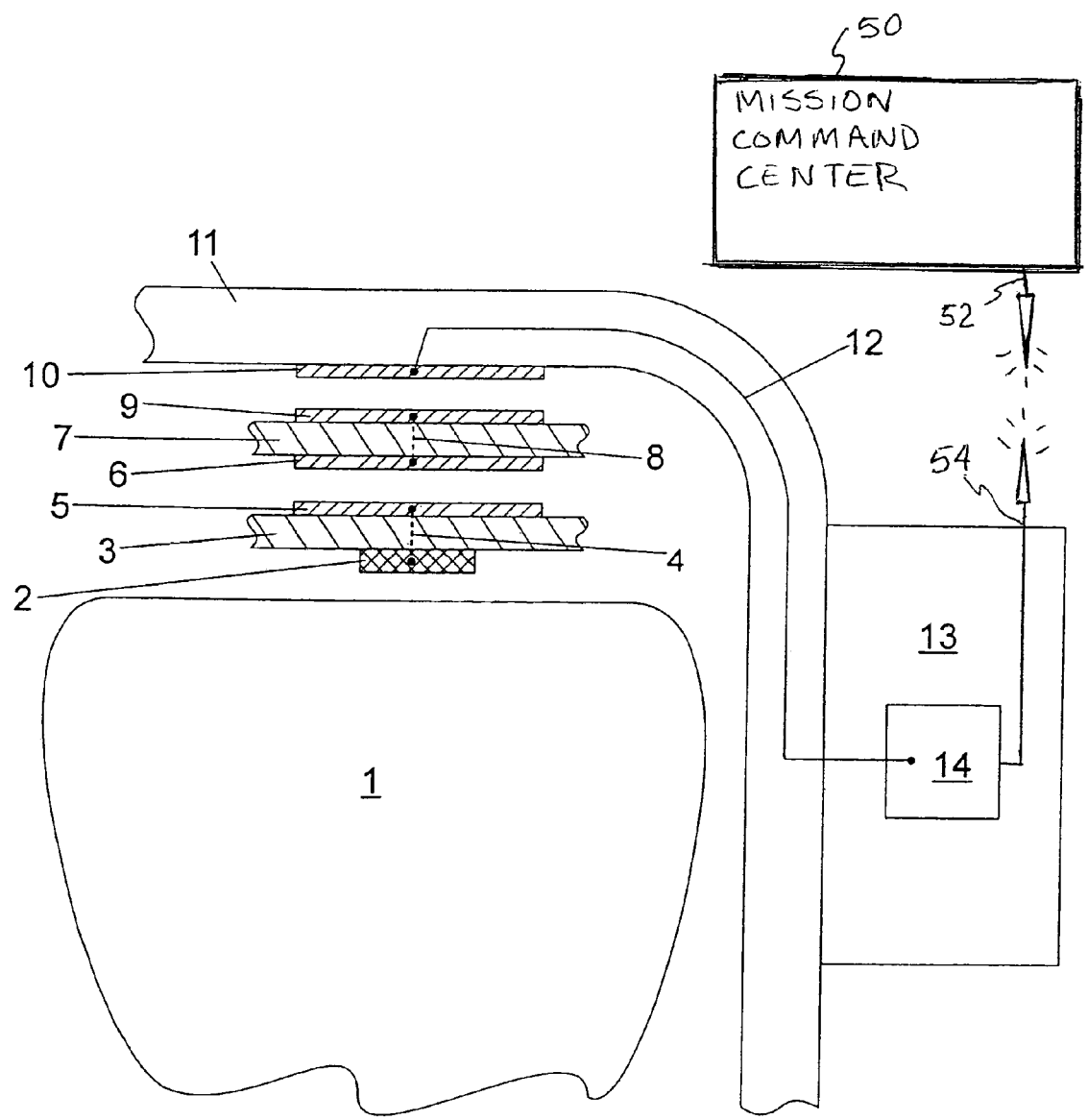

Referring to the drawings in particular, The layers of clothing 3, 7 shown schematically and optionally additional layers of clothing, which are associated with corresponding pieces of clothing, are equipped with an electric line connection 4, 8 between the top side and the underside. The electric line connection 4, 8 through the layers of clothing 3, 7 and optionally additional layers of clothing is embodied especially by electrically conductive threads, plug-in elements or push contact elements, which contact through one or more layers of clothing 3, 7. As an alternative, the layers of clothing 3, 7 are provided with holes or cut-out patterns, so that the electrode 2 and/or the electrically conductive surfaces (5, 6, 9, 10) can be electrically contacted through the layers of clothing 3, 7 to form the line connection 4, 8.

The lowermost layer of clothing 3 is provided with an electrode 2, especially a reference electrode, which contacts the skin surface of the body of the wearer of the clothing.

The lowermost layer of clothing 3 is provided with an electrically conductive surface 5 on the side facing away from the skin surface. The layer of clothing 7 lying over it and optionally additional layers of clothing are provided with an electrically conductive surface 6, 9 on the underside and the top side each, which said conductive layer is oriented such that an at least partial overlap and contacting of the respective conductive surfaces located directly opposite each other, for example, 5 and 6 in case of two layers of clothing 3 and 7, is ensured during the wearing of the layers of clothing. In particular, the conductive surfaces are structured or designed in the form of Velcro fasteners, so that the position of the individual layers of clothing in relation to one another and of the conductive surfaces is fixed. A carrying belt 11 with another conductive surface 10 directed toward the body is finally led over the stack of at least two layers of clothing 3, 7. A cable forming an electric line 12 in the carrying belt 11 is connected with an evaluating unit 14, which is located, for example, in or at a respirator 13. The evaluating unit 14 communicates especially with a mission command center 50 in a wireless manner (via transceivers 52 and 54 for wireless communication). By pressing on the carrying belt 11 mechanically, which is brought about by the weight of the respirator 13, the electrode 2 is in contact with the skin surface of the body 1 and a good contact is established between the conductive surfaces 5, 6, 9, 10 of the individual layers of clothing 3, 7 up to the carrying belt 11. Sufficiently good electric contact is thus established even in case of the harsh conditions of a firefighting mission.

While specific embodiments of the invention have been shown and described in detail to illustrate the application of the principles of the invention, it will be understood that the invention may be embodied otherwise without departing from such principles.

What is claimed is:

1. A device for transmitting an electric signal detected by contact with the skin surface of the wearer to an evaluating unit, the device comprising:
   a stack of at least two layers of clothing with an electric line connection through each of the layers of clothing, said layers of clothing including a lowermost layer of the clothing adjacent to the skin of the wearer and one or more additional layer of the clothing;
   an electrode contacting the skin surface of the body of the wearer of the clothing, said lowermost layer of the clothing being provided with said electrode;
   an electrically conductive surface on a side of said lowermost layer of the clothing facing away from the skin surface;
   an electrically conductive surface on an underside of each said one or more additional layer of the clothing; and
   an electrically conductive surface on a top side of each said one or more additional layer of the clothing;
   a carrying belt led over the stack of said layers of clothing;
   a belt electrically conductive surface, said carrying belt provided with said belt electrically conductive surface facing a topmost layer of clothing;
   an evaluating unit; and
   an electric line connecting said belt electrically conductive surface with said evaluating unit.

2. A device in accordance with claim 1, wherein the carrying belt is connected to a respirator on the back of the wearer of the clothing, so that the weight of the respirator presses the carrying belt onto the stack of said layers of clothing.

3. A device in accordance with claim 1, further comprising at least one additional electrode to provide a plurality of electrodes wherein said lowermost layer of clothing is provided with said plurality of electrodes, wherein one of said electrodes is a reference electrode for an ECG measurement.

4. A device in accordance with claim 1, wherein each of said electrically conductive surfaces have a size of a few square cm and are oriented such that they overlap at least partially when the pieces of clothing associated with the layers of clothing are put on by the wearer of the clothing.

5. A device in accordance with claim 1, wherein the electric line is integrated within the carrying belt.

6. A device in accordance with claim 1, further comprising a mission command center wherein the evaluating unit is operatively connected to said mission command center in a wireless manner.

7. A device in accordance with claim 1, wherein said electrically conductive surfaces comprise one of a bonded structure, a welded structure, a sintered structure, a woven structure, an embroidered structure, a knitted structure and a tufted structure.

8. A device in accordance with claim 1, said electrically conductive surfaces are structured or designed in the form of Velcro fasteners, so that the position of the individual layers of clothing and of the carrying belt in relation to one another and to the conductive surfaces can be fixed.

9. A device in accordance with claim 1, wherein electrically conductive threads, plug-in or push contact elements, which contact through one or more said layers of clothing, are provided for the electric line connection through the layers of clothing.

10. A device in accordance with claim 1, wherein for the electric line connection through the layers of clothing, the clothing is provided with holes or with cut-out patterns, so that the electrode and/or the electrically conductive surfaces can be electrically contacted through the layers of clothing.

11. A device for transmitting an electric signal detected by contact with the skin surface of the wearer to an evaluating unit, the device comprising:
   a skin adjacent layer of clothing adjacent to the skin of the wearer;
   an electrode contacting the skin surface of the body of the wearer of the clothing, said skin adjacent layer of the clothing being provided with said electrode;
   a skin adjacent clothing layer electrically conductive surface on a side of said skin adjacent layer of clothing facing away from said skin surface;

a skin adjacent clothing layer electric path from said skin adjacent clothing layer electrically conductive surface to said electrode;

an additional layer of the clothing cooperating with said skin adjacent layer of clothing to form layered clothes;

an inner additional clothing layer electrically conductive surface on an inner side of said additional layer of the clothing;

an outer additional clothing layer electrically conductive surface on an outer side of said additional layer of the clothing;

an additional layer electric path from said inner additional clothing layer electrically conductive surface to said outer additional clothing layer electrically conductive surface;

an evaluating unit; and an electrical connection with an associated electrical connection connecting said outer additional clothing layer electrically conductive surface with said evaluating unit.

12. A device in accordance with claim 11, further comprising:

a carrying belt positioned over said layered clothes, said electrical connection associated with said electrical connection comprising a belt electrically conductive surface, said carrying belt provided with said belt electrically conductive surface facing the layered clothes;

a respirator, wherein said carrying belt is connected to said respirator on the back of the wearer of the clothing, so that the weight of the respirator presses the carrying belt onto the layered clothes.

13. A device in accordance with claim 11, further comprising at least one additional electrode to provide a plurality of electrodes wherein said skin adjacent layer of clothing is provided with said plurality of electrodes, wherein one of said electrodes is a reference electrode for an ECG measurement.

14. A device in accordance with claim 11, wherein each said electrically conductive surface has a size of a few square cm and is oriented positioned overlapping at least partially with an adjacent electrically conductive surface of the layered clothes.

15. A device in accordance with claim 12, wherein the electric line is integrated within the carrying belt.

16. A device in accordance with claim 11, further comprising a mission command center wherein the evaluating unit is connected to said mission command center via wireless transceivers.

17. A device in accordance with claim 11, wherein said electrically conductive surfaces comprise one of a bonded structure, a welded structure, a sintered structure, a woven structure, an embroidered structure, a knitted structure and a tufted structure.

18. A device in accordance with claim 11, said electrically conductive surfaces are structured or designed in the form of hook and loop fasteners or with an adjacent hook and loop fastener, so that the position of the individual layers of clothing and of the carrying belt in relation to one another and to the conductive surfaces can be fixed.

19. A device in accordance with claim 11, wherein electrically conductive threads, plug-in or push contact elements, which contact through one or more said layers of clothing, are provided for the electric path through the layers of clothing and/or for the electric path through the layers of clothing, the clothing is provided with holes or with cut-out patterns, so that the electrode and/or the electrically conductive surfaces can be electrically contacted through the layers of clothing.

20. A method of transmitting an electric signal detected by contact with the skin surface of the wearer to an evaluating unit, the method comprising:

providing a skin adjacent layer of clothing with an electrode for contacting the skin surface of the body of the wearer of the clothing and with a skin adjacent clothing layer electrically conductive surface on a side of said skin adjacent layer of clothing facing away from said skin surface and with a skin adjacent clothing layer electric path from said skin adjacent clothing layer electrically conductive surface to said electrode;

donning the skin adjacent layer of clothing by the wearer to be adjacent to the skin of the wearer with the electrode contacting the skin surface of the body of the wearer;

providing an additional layer of the clothing with an inner additional clothing layer electrically conductive surface on an inner side of said additional layer of the clothing and with an outer additional clothing layer electrically conductive surface on an outer side of said additional layer of the clothing and with an additional layer electric path from said inner additional clothing layer electrically conductive surface to said outer additional clothing layer electrically conductive surface;

donning the additional layer of the clothing by the wearer so the skin adjacent layer and the additional layer cooperate to form layered clothes with an electrically conductive path from said electrode to said outer additional clothing layer electrically conductive surface;

providing an evaluating unit; and providing an electrical connection connecting said outer additional clothing layer electrically conductive surface with said evaluating unit.

* * * * *